(12) United States Patent
Hedrick et al.

(10) Patent No.: US 8,492,504 B2
(45) Date of Patent: Jul. 23, 2013

(54) CATALYTIC DEPOLYMERIZATION OF POLYMERS CONTAINING ELECTROPHILIC LINKAGES USING NUCLEOPHILIC REAGENTS

(75) Inventors: James Lupton Hedrick, Pleasanton, CA (US); Russell Clayton Pratt, Oakland, CA (US); Robert M. Waymouth, Palo Alto, CA (US)

(73) Assignees: International Business Machines Corporation, Armonk, NY (US); The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/569,033

(22) Filed: Aug. 7, 2012

(65) Prior Publication Data

US 2012/0302781 A1 Nov. 29, 2012

Related U.S. Application Data

(62) Division of application No. 12/496,520, filed on Jul. 1, 2009, now Pat. No. 8,309,618.

(51) Int. Cl.
*C08G 63/00* (2006.01)

(52) U.S. Cl.
USPC .......... 528/274; 528/86; 528/198; 528/308.1; 528/310; 521/40; 521/48; 502/150; 502/162; 548/336.5; 544/247; 544/281; 564/230; 564/238; 564/241; 564/242

(58) Field of Classification Search
USPC .................... 521/40, 40.5, 41, 42.5, 43.5, 44, 521/44.5, 46, 46.5, 47, 47.5, 48, 48.5, 49, 521/49.5, 49.8, 42; 560/1, 8, 76, 89; 525/50, 525/418, 419, 437; 528/86, 88, 271, 272, 528/274, 308.1, 310, 332, 480, 486, 491, 528/492, 493, 494, 495, 496, 497, 498, 502 R, 528/503; 502/150, 162; 548/336.5; 544/247; 544/281; 564/230, 238, 241, 242
See application file for complete search history.

(56) References Cited

U.S. PATENT DOCUMENTS

| 3,254,054 | A | 5/1966 | Boerma |
| 4,652,667 | A | 3/1987 | Green |
| 4,681,967 | A | 7/1987 | Green |
| 4,797,487 | A | 1/1989 | A'Court |

(Continued)

FOREIGN PATENT DOCUMENTS

EP 629645 6/1994

OTHER PUBLICATIONS

"Modern Polyesters: Chemistry and Technology of Polyesters and Copolyesters", 2003, John Wiley and Sons, Ltd., p. 90.*

(Continued)

*Primary Examiner* — Frances Tischler
(74) *Attorney, Agent, or Firm* — Karen Canaan; CanaanLaw, P.C.

(57) ABSTRACT

The disclosure relates to methods and materials useful for depolymerizing a polymer. In one embodiment, for example, the disclosure provides a method for depolymerizing a polymer containing electrophilic linkages, wherein the method comprises contacting the polymer with a nucleophilic reagent in the presence of a guanidine-containing compound. The methods and materials of the disclosure find utility, for example, in the field of waste reclamation and recycling.

15 Claims, 1 Drawing Sheet

U.S. PATENT DOCUMENTS

| | | | |
|---|---|---|---|
| 5,418,316 | A | 5/1995 | Kuhling et al. |
| 5,559,159 | A | 9/1996 | Sublett et al. |
| 6,136,869 | A | 10/2000 | Ekart et al. |
| 6,646,103 | B1 | 11/2003 | Le Perchec et al. |
| 6,911,546 | B2 | 6/2005 | Hedrick et al. |
| 6,916,936 | B2 | 7/2005 | Hedrick et al. |
| 6,969,705 | B2 | 11/2005 | Pecquet et al. |
| 7,544,800 | B2 | 6/2009 | Hedrick et al. |
| 2005/0049418 | A1 | 3/2005 | Hedrick et al. |
| 2011/0003949 | A1 | 1/2011 | Hedrick et al. |

OTHER PUBLICATIONS

Alleman et al., Theory of Asymmetic Organoctalysis of Aldol and Related Reactions: Rationalizations and Predictions, Acc. Chem. Res. 37(8):558-569 (2004).

Barbas III, Organocatalysis Lost: Modern Chemistry, Ancient Chemistry, and an Unseen Biosynthetic Apparatus, Angew. Chem. Int. Ed. Engl. 47(1):42-47 (2008).

Bertelsen & Jorgensen, Organocatalysis—After the Gold Rush, Chem. Soc. Rev. 38(8):2178-2189 (2009).

Chuma et al., The Reaction Mechanism for the Organocatalytic Ring-Opening Polymerization of L-Lactide Using a Guanidine-Based Catalyst: Hydrogen-Bonded or Covalently Bonded? J. Am. Chem. Soc. 130(21):6749-6754 (2008).

Cowan et al., On the Interaction Between N-Heterocyclic Carbenes and Organic Acids: Structural Authentication of the First N-H . . . C Hydrogen Bond and Remarkably Short C-H . . . O Interactions, Angew. Chem. Int. Ed. Engl. 41 (8):1432-1434 (2002).

Culkin et al., Zwitterionic Polymerization of Lactide to Cyclic Poly(Lactide) by Using N-Heterocyclic Carbene Organocatalysts, Angew. Chem. Int. Ed. Engl. 46(15):2627-2630 (2007).

Grasa et al., N-Heterocyclic Carbenes as Versatile Nucleophilic Catalysts for Transesterification/Acylation Reactions, Org. Lett. 4(21):3583-3586 (2002).

Hajos & Parish, Assymetic Synthesis of Bicyclic Intermediates of Natural Product Chemistry, J. Org. Chem. 39 (12):1615-1621 (1974).

Jeong et al., Zwitterionic Polymerization: A Kinetic Strategy for the Controlled Synthesis of Cyclic Polylactide, J. Am. Chem. Soc. 131(13):4884-4891 (2009).

Kiesewetter et al., Cyclic Guanidine Organic Catalysts: What is Magic About Triazabicyclodecene? J. Org. Chem. 74(24):9490-9496 (2009).

Lai et al., Theoretical Study on the Mechanism of N-Heterocyclic Carbene Catalyzed Transesterification Reactions, Tetrahedron Lett. 46:6265-6270 (2005).

List, Introduction: Organoctalysis, Chem. Rev. 107(12):5413-5415 (2007).

Lohmeijer et al., Guanidine and Amidine Organo-Catalysts for Ring-Opening Polymerization of Cyclic Ester Molecules, Macromolecules 39:8574-8583 (2006).

Lohmeijer et al., Organocatalytic Living Ring-Opening Polymerization of Cyclic Carboxysilanes, Organic Letters 8:4683-4686 (2006).

Movassaghi & Schmidt, N-Heterocyclic Carbene-Catalyzed Amidation of Unactivated Esters with Amino Alcohols, Org. Lett. 7(12):2453-2456 (2005).

Nederberg et al., Organocatalytic Ring Opening Polymerization of Trimethylene Carbonate, Biomacromolecules 8(1):153-160 (2007).

Pratt et al., Triazabicyclodecene: A Simple Bifuncitonal Organocatalyst for Acyl Transfer and Ring-Opening Polymerization of Cyclic Esters, J. Am. Chem. Soc. 128:4556-4557 (2006).

Schuchardt et al., Transesterification of Vegetable Oils: A Review, J. Braz. Chem. Soc. 9(1):199-210 (1998).

Schwesinger et al., Extremely Strong Uncharged Auxiliary Bases; Monomeric and Polymer-Supported Polyaminophosphazenes (P2-P5), Liebigs Ann. 1055-1081 (1996).

Spivey & Arseniyadis, Nucleophilic Catalysis by 4-(Dialkylamino)pyridines Revisited—The Search for Optimal Reactivity and Selectivity, Agnew. Chem. Int. Ed. Engl. 43(41):5436-5441 (2004).

\* cited by examiner

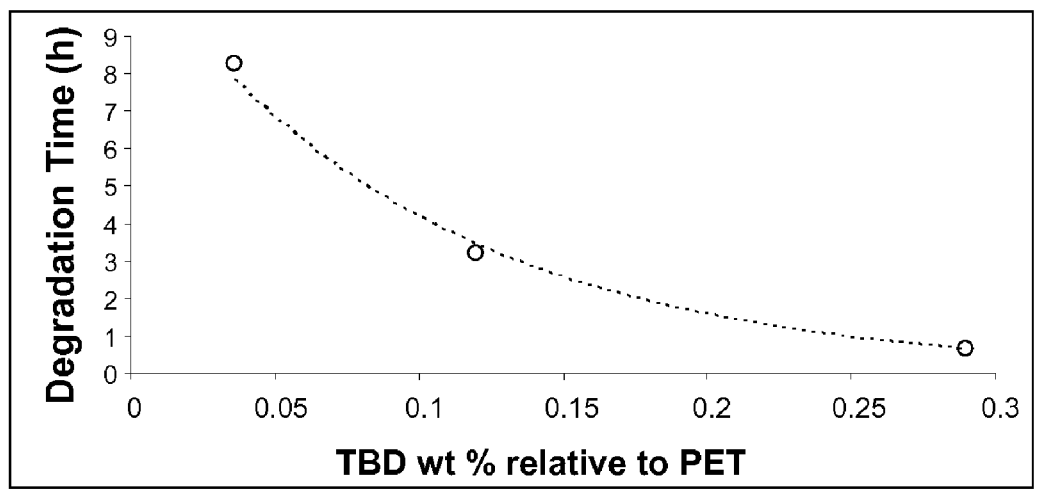

CATALYTIC DEPOLYMERIZATION OF POLYMERS CONTAINING ELECTROPHILIC LINKAGES USING NUCLEOPHILIC REAGENTS

CROSS-REFERENCE TO RELATED APPLICATIONS

This application is a divisional of U.S. patent application Ser. No. 12/496,520, filed on Jul. 1, 2009, the disclosure of which is incorporated in its entirety herein.

ACKNOWLEDGEMENT OF GOVERNMENT SUPPORT

This invention was made with Government support under contract CHE 0645891 awarded by the National Science Foundation. The government has certain rights in this invention.

TECHNICAL FIELD

This invention relates generally to the depolymerization of polymers, and, more particularly relates to an organocatalytic method for depolymerizing polymers using nucleophilic reagents. The invention is applicable in numerous fields, including industrial chemistry and chemical waste disposal, plastics recycling, and manufacturing processes requiring a simple and convenient method for the degradation of polymers.

BACKGROUND OF THE INVENTION

Technological advances of all kinds continue to present many complex ecological issues. Consequently, waste management and pollution prevention are two very significant challenges of the 21$^{st}$ century. The overwhelming quantity of plastic refuse has significantly contributed to the critical shortage of landfill space faced by many communities. For example, poly(ethylene terephthalate (PET) (poly(oxy-1,2-ethanediyl-oxycarbonyl-1,4-diphenylenecarbony-1), a widely used engineering thermoplastic for carpeting, clothing, tire cords, soda bottles and other containers, film, automotive applications, electronics, displays, etc. will contribute more than 1 billion pounds of waste to land-fills in 2002 alone. The worldwide production of PET continues to grow at a high rate. Interestingly, the precursor monomers represent a small amount of the petrochemical stream. Moreover, the proliferation of the use of organic solvents, halogenated solvents, water, and energy consumption in addressing the need to recycle commodity polymers such as PET and other polyesters has created the need for environmentally responsible and energy efficient recycling processes. See Nadkarni (1999) International Fiber Journal 14(3).

Commercial synthesis of PET often involves a two-step transesterification process from dimethyl teraphthalate (DMT) and excess ethylene glycol (EO) in the presence of a metal alkanoates or acetates of calcium, zinc, manganese, titanium etc. This first step generates bis(hydroxy ethylene) teraphthalate (BHET) with the elimination of methanol and the excess EO. The BHET is heated, generally in the presence of a transesterification catalyst, to generate high polymer. This process is generally accomplished in a vented extruder to remove the polycondensate (EO) and generate the desired thermoformed object from a low viscosity precursor.

Effort has been invested in researching recycling strategies for PET, and these efforts have produced three commercial options; mechanical, chemical and energy recycling. Energy recycling simply burns the plastic for its calorific content. Mechanical recycling, the most widespread approach, often involves grinding the polymer to powder, which is then mixed with "virgin" PET. See Mancini et al., Materials Research 2(1):33-38 (1999). Many chemical companies use this process in order to recycle PET; however, it has been demonstrated that successive recycling steps cause significant polymer degradation, in turn resulting in a loss of desirable mechanical properties.

Recycling using chemical degradation involves a process that depolymerizes a polymer to starting material, or at least to relative short oligomeric components. Industrial processes for chemical recycling include glycolysis, methanolysis, and hydrolysis. It is known that methanolysis and glycolysis may be carried out using a catalyst comprising an N-heterocyclic carbene (NHC).

Methanolysis

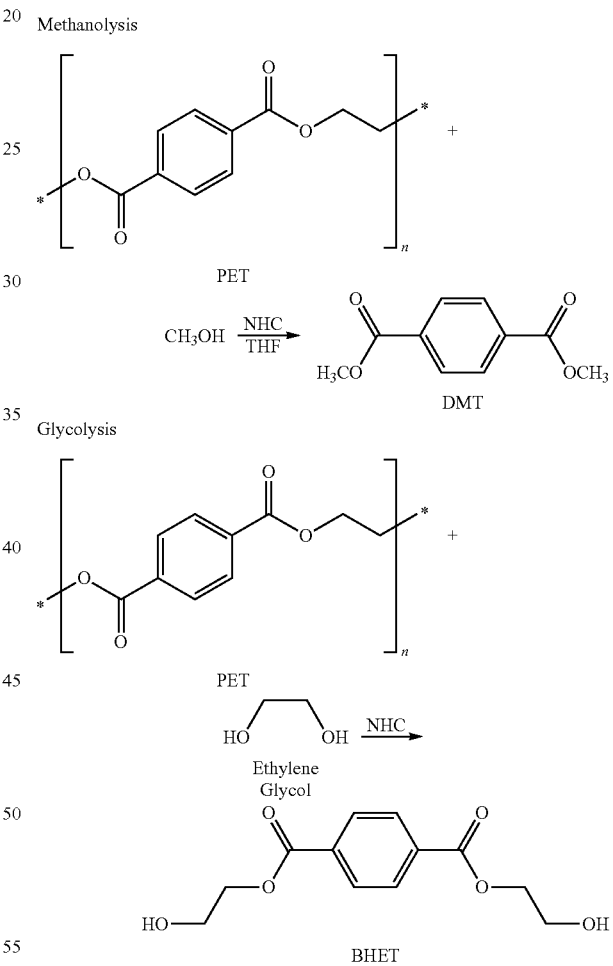

Glycolysis

Chemical recycling processes are the most difficult to control, since in many cases elevated temperature and pressure are required along with a catalyst composed of a strong base, an organometallic complex, and/or a carbene compound. See Sako et al., Proc. of the 4$^{th}$ Int'l Symposium on Supercritical Fluids, pp. 107-110 (1997). In many instances, the use of such catalysts result in significant quantities of undesirable byproducts; such materials are generally unsuitable, for example, for use in medical materials or food packaging, limiting their utility. Also, where large amounts of energy are required to effect depolymerization, sustainability arguments for chemical depolymerization are essentially eliminated. Furthermore, some depolymerization catalysts are difficult to prepare, unstable to long-term storage, or require stringent reaction conditions; therefore, currently the chemical recycling of PET is not economically viable relative to mechanical recycling and is thus not widely practiced.

In addition, the low cost of starting monomer provides significant economic challenges for alternative technologies utilizing post-consumer PET as a feedstock. Incentives to develop better processes for chemical recycling remain high due to PET's increasing consumer use, the subsequent landfill disposal problem and PET's slow rate of natural degradation. Efforts in the chemical recycling of PET are thus ideally focused on developing an environmentally safe, economically feasible, and industrially applicable process for widescale application. Moreover, chemical recycling methodologies that are energy efficient and do not involve a heavy metals are highly desirable.

SUMMARY OF THE INVENTION

Accordingly, there is a need in the art for improved depolymerization methods that would, for example, involve mild reaction conditions, non-metallic catalysts, and/or easy to obtain, stable catalysts.

The invention provides an efficient catalytic depolymerization reaction that employs mild conditions, wherein production of undesirable byproducts resulting from polymer degradation is minimized. The reaction can be carried out in solution or in the melt using an excess of the nucleophilic reagent. In solution, the reaction can be carried out at temperatures of 80° C. or less, and, because a nonmetallic catalyst is preferably employed, the depolymerization products, in a preferred embodiment, are substantially free of metal contaminants. With many of the catalysts disclosed herein, the depolymerization reaction can be carried out at a temperature of at most 60° C. or even 30° C. or lower, i.e., at room temperature. Furthermore, in preferred embodiments, the catalysts are substantially stable under ambient conditions (e.g., atmospheric temperature and pressure). When a solvent is not used, the reaction can be carried out at temperatures up to about 200° C., or ranging from about 120° C. to 200° C.

More specifically, in one aspect of the invention, a method is provided for depolymerizing a polymer having a backbone containing electrophilic linkages, wherein the method involves contacting the polymer with a nucleophilic reagent and a catalyst at a temperature of less than 80° C. when performed in solution or below 200° C. when performed in the melt. An important application of this method is in the depolymerization of polyesters, including homopolymeric polyesters (in which all of the electrophilic linkages are ester linkages) and polyester copolymers (in which a fraction of the electrophilic linkages are ester linkages and the remainder of the electrophilic linkages are other than ester linkages).

In a related aspect of the invention, a method is provided for depolymerizing a polymer having a backbone containing electrophilic linkages, wherein the method involves contacting the polymer with a nucleophilic reagent and a catalyst that yields depolymerization products that are substantially free of metal contaminants. The polymer may be, for example, a polyester, a polycarbonate, a polyurethane, or a related polymer, in either homopolymeric or copolymeric form, as indicated above. In this embodiment, in order to provide reaction products that are substantially free of contamination by metals and metal-containing compounds, the catalyst used is a purely organic, nonmetallic catalyst.

Preferred catalysts herein are guanidine-containing compounds. For example, preferred catalysts are cyclic guanidines, including monocyclic and polycyclic guanidines. Polycyclic guanidines suitable for the methods of the disclosure include fused and non-fused polycyclic compounds. Further details of suitable cyclic guanidine catalysts are provided below.

As alluded to above, one important application of the present invention is in the recycling of polyesters, including, by way of illustration and not limitation: PET; poly(butylene terephthalate) (PBT); poly(alkylene adipate) and their copolymers; and poly(ε-caprolactone). The methodology of the invention provides an efficient means to degrade such polymers into their component monomers, derivatives of such, and/or relatively short oligomeric fragments without need for metallic catalysts, extreme reaction conditions, or stringent precautions to prevent decay of the catalyst.

In one embodiment, the disclosure provides a method for depolymerizing a polymer. The method comprises contacting a polymer having a backbone comprising electrophilic linkages with a nucleophilic reagent in the presence of a guanidine-containing compound.

In another embodiment, the disclosure provides a composition comprising a polymer, a nucleophilic compound, and a guanidine-containing compound. The polymer has a backbone that comprises a repeat unit with an electrophilic linkage.

In a still further embodiment, the disclosure provides an improved method for depolymerizing a polymer having a backbone comprising electrophilic linkages. The improvement comprises contacting the polymer with a nucleophile in the presence of a guanidine-containing compound.

BRIEF DESCRIPTION OF THE DRAWINGS

FIG. 1 represents recorded degradation times required for a complete dissolution of PET with respect to the weight amounts of TBD.

DETAILED DESCRIPTION OF THE INVENTION

Unless otherwise indicated, this invention is not limited to specific polymers, catalysts, nucleophilic reagents, or depolymerization conditions. The terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a polymer" encompasses a combination or mixture of different polymers as well as a single polymer, reference to "a catalyst" encompasses both a single catalyst as well as two or more catalysts used in combination, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a linear, branched, or cyclic saturated hydrocarbon group (i.e., a mono-radical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein may, for example, may contain 1 to 3 carbon atoms, and as a further example, such substituents may contain 1 or 2 carbon atoms (i.e., methoxy and ethoxy). The term "alkylthio" as used herein refers to a group —S-alkyl, where "alkyl" is as defined above.

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "alkylene" as used herein refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing "Lower alkylene" refers to alkylene linkages containing from 1 to 6 carbon atoms. Examples include, methylene (—$CH_2$—), ethylene (—$CH_2CH_2$—), propylene (—$CH_2CH_2$—), 2-methylpropylene (—$CH_2$—$CH(CH_3)$—$CH_2$—), hexylene (—$(CH_2)_6$—) and the like.

Similarly, the terms "alkenylene," "alkynylene," "arylene," "aralkylene," and "alkarylene" as used herein refer to di-radical alkenyl, alkynyl, aryl, aralkyl, and alkaryl groups, respectively.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted, unsubstituted, and/or heteroatom-containing hydrocarbyl moieties. The term "hydrocarbylene" refers to a di-radical hydrocarbyl group.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-substituted $C_1$-$C_{24}$ alkylcarbamoyl (—(CO)—$NH(C_1$-$C_{24}$ alkyl)), di-substituted alkylcarbamoyl (—(CO)—$N(C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—$N^+$≡$C^-$), cyanato (—O—C≡N), isocyanato (—O—$N^+$=$C^-$), isothiocyanato (—S—C≡N), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)($OH)_2$), phosphonato (—P(O)($O^-)_2$), phosphinato (—P(O)($O^-$)), phospho (—$PO_2$), and phosphino (—$PH_2$), mono- and di-($C_1$-$C_{24}$ alkyl)-substituted phosphino, mono- and di-($C_5$-$C_{20}$ aryl)-substituted phosphino; and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl and aryl" is to be interpreted as "substituted alkyl and substituted aryl."

Unless otherwise specified, the terms "guanidine compound," "guanidine catalyst," "guanidine-containing compound," and the like refer to compounds containing a guanidinyl moiety, i.e., compounds containing the structure

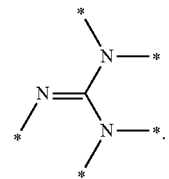

Unless otherwise specified, reference to an atom is meant to include isotopes of that atom. For example, reference to H is meant to include $^1$H, $^2$H (i.e., D) and $^3$H (i.e., T), and reference to C is meant to include $^{12}$C and all isotopes of carbon (such as $^{13}$C).

By "substantially free of" a particular type of chemical compound is meant that a composition or product contains less 10 wt % of that chemical compound, for example less than 5 wt %, or less than 1 wt %, or less than 0.1 wt %, or less than 0.01 wt %, or less than 0.001 wt %. For instance, in preferred embodiments the depolymerization products herein are "substantially free of" metal contaminants, including metals per se, metal salts, metallic complexes, metal alloys, and organometallic compounds.

Accordingly, the invention features a method for depolymerizing a polymer having a backbone containing electrophilic linkages. The electrophilic linkages may be, for example, ester linkages (—(CO)—O—), carbonate linkages (—O—(CO)—O)—, urethane linkages (—O—(CO)—NH), substituted urethane linkages (—O—(CO)—NR—, where R is a nonhydrogen substituent such as alkyl, aryl, alkaryl, or the like), amido linkages (—(CO)—NH—), substituted amido linkages (—(CO)—NR— where R is as defined previously), thioester linkages (—(CO)—S—), sulfonic ester linkages (—S(O)$_2$—O—), ketone linkages (—C(=O)—), and the like. The polymer undergoing depolymerization may be linear, branched, hyperbranched, dendritic, cyclic, comb-shaped, star-shaped, or other such architecture, and may be a homopolymer or copolymer, the latter including random, block, multiblock, and alternating copolymers, terpolymers, and the like.

Examples of polymers that can be depolymerized using the methodology of the invention include, without limitation: poly(alkylene terephthalates) such as poly(ethylene terephthalate) (PET), fiber-grade PET (a homopolymer made from monoethylene glycol and terephthalic acid), bottle-grade PET (a copolymer made based on monoethylene glycol, terephthalic acid, and other comonomers such as isophthalic acid, cyclohexene dimethanol, etc.), poly(butylene terephthalate) (PBT), and poly(hexamethylene terephthalate); poly (alkylene adipates) such as poly(ethylene adipate), poly(1,4- butylene adipate), and poly(hexamethylene adipate); poly (alkylene suberates) such as poly(ethylene suberate); poly (alkylene sebacates) such as poly(ethylene sebacate); poly(ε-caprolactone) and poly(β-propiolactone); poly(alkylene isophthalates) such as poly(ethylene isophthalate); poly (alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1, 4-cyclohexanediyl alkylene dicarboxylates) such as poly (trans-1,4-cyclohexanediyl ethylene dicarboxylate); poly(1, 4-cyclohexane-dimethylene alkylene dicarboxylates) such as poly(1,4-cyclohexane-dimethylene ethylene dicarboxylate); poly([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly (tetramethylglycolide), and poly(lactide-co-glycolide); and polycarbonates of bisphenol A, 3,3'-dimethylbisphenol A, 3,3',5,5'-tetrachlorobisphenol A, 3,3',5,5'-tetramethylbisphenol A; polyamides such as poly(p-phenylene terephthalamide) (KEVLAR®); poly(alkylene carbonates) such as polypropylene carbonate); polyurethanes such as those available under the tradenames BAYTEC® and BAYFIL®, from Bayer Corporation; and polyurethane/polyester copolymers such as that available under the tradename BAYDAR®, from Bayer Corporation.

Thus, in some embodiments, the polymers that can be depolymerized according to the methods disclosed herein comprise repeat units having the structure [-$L^1$-$E^1$-], [-$L^1$-$E^1$-$L^2$-], or [-$E^1$-$L^1$-$E^2$-], wherein $L^1$ and $L^2$ are independently selected from linker moieties and $E^1$ and $E^2$ are independently selected from electrophilic linkage. Preferred linker moieties are $C_1$-$C_{30}$ hydrocarbylene groups. For example, linker moieties include substituted and unsubstituted $C_1$-$C_{30}$ alkylene, $C_2$-$C_{30}$ alkenylene, $C_2$-$C_{30}$ alkynylene, $C_5$-$C_{30}$ arylene, $C_6$-$C_{30}$ alkenylene, and $C_6$-$C_{30}$ aralkylene, any of which may be heteroatom-containing and/or halogenated (including, for example, perfluorinated or perchlorinated). Linker moieties may also be heteroatom groups, including thioether (—S—), ether (—O—), and amino (—NR—) groups. Preferred electrophilic linkages are any of those described above.

The polymers for depolymerization may be obtained from any suitable source, and in particularly preferred embodiments, the polymers are obtained as post-consumer waste to be recycled. For example, the polymers may be obtained from used consumable plastic goods such as those used in beverage containers, food containers, other liquid containers, packaging such as blister packaging, and synthetic fibers.

Depolymerization of the polymer is carried out, as indicated herein, in the presence of a nucleophilic reagent and a catalyst. Nucleophilic reagents are those that comprise one or more nucleophilic groups, such as hydroxyl, ether, carboxylato (e.g., —COO⁻), amine, azide, sulfhydryl, and the like. Nucleophilic reagents therefore include monohydric alcohols, diols, polyols, amines, diamines, polyamines, sulfhydryls, disulfhydryls, polysulfhydryls, and combinations thereof, such as amino alcohols and sulfhydryl alcohols.

In some embodiments, the nucleophilic reagent consists of a single nucleophilic group, and has the structure R-$Nu^1$, wherein R is a $C_1$-$C_{30}$ hydrocarbyl group and $Nu^1$ is any of the nucleophilic groups previously described.

In some embodiments, nucleophilic reagents comprise two nucleophilic groups separated by a linker, and have the structure $Nu^1$-$L^1$-$Nu^2$, wherein $Nu^1$ is as described previously, $Nu^2$ is a nucleophilic group (such as those described for $Nu^1$) and wherein $L^1$ is as described previously. Examples of such difunctional nucleophilic reagents include alkyl diols, aryl diols, alkyl diamines, aryl diamines, amino alcohols, amino thiols, and the like.

In some embodiments, the nucleophilic reagent comprises three nucleophilic groups, and has the structure

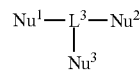

(also written $Nu^1$-$L^3$($Nu^2$)$Nu^3$) wherein $Nu^1$ and $Nu^2$ are as described previously, $Nu^3$ is a nucleophilic group (such as those described for $Nu^1$), and $L^3$ may be any of the linkers described previously for $L^1$, provided that linker $L^3$ has at least three non-hydrogen substituents (i.e., $Nu^1$-$Nu^3$).

Any combination of nucleophilic reagents (having the same or a different number of nucleophilic groups) may be used. The nucleophilic reagent is selected to correspond to the particular electrophilic linkages in the polymer backbone, such that nucleophilic attack at the electrophilic linkage results in cleavage of the linkage. For example, a polyester can be cleaved at the ester linkages within the polymer backbone using an alcohol, preferably a $C_1$-$C_{12}$ monohydric or dihydric alcohol such as methanol, ethanol, isopropanol, t-butyl alcohol, ethylene glycol, propylene glycol, and the like. It is believed that such a reaction cleaves the ester linkages via a transesterification reaction. In another example, depolymerization of a polyester can be carried out using a catalyst and an amine as the nucleophilic reagent, wherein the depolymerization occurs via catalytic amidation.

In some embodiments, the number of nucleophilic groups will be present in excess of the number of electrophilic groups in the polymer to be depolymerized at the beginning of the reaction. In some other embodiments, the ratio of nucleophilic groups to electrophilic groups is 1:1. In cases where it is desired to stop the depolymerization reaction prior to complete depolymerization (i.e., prior to substantially 100% reaction of the electrophilic groups in the polymer), a ratio of less than 1:1 (nucleophilic groups to electrophilic groups) may be used.

A few specific examples of suitable nucleophilic groups include methanol, ethanol, propanol, butanol, ethylene glycol, propylene glycol, methylamine, ethylamine, ethylenediamine, propylenediamine, methanethiol, ethanethiol, as well as the following:

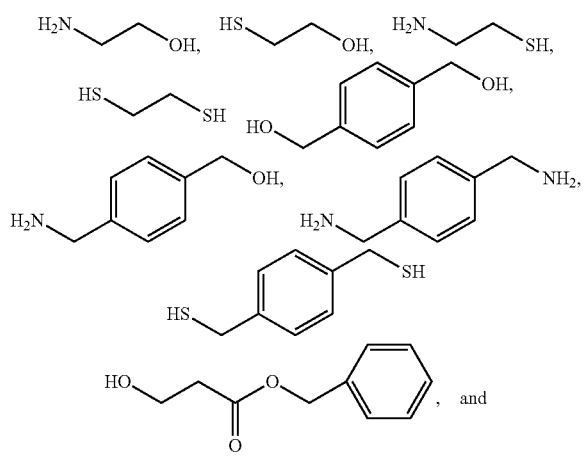

-continued

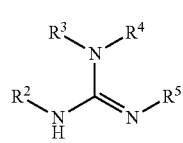

The preferred catalysts for the polymerization reactions are organic compounds containing a guanidine moiety. In some preferred embodiments, the polymerization catalysts are organic guanidines having the structure of formula (I)

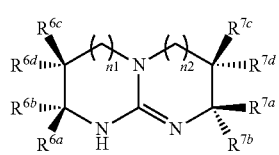

(I)

wherein $R^2$, $R^3$, $R^4$ and $R^5$ are independently selected from hydrogen and $C_1$-$C_{30}$ hydrocarbyl, provided that any two of $R^2$, $R^3$, $R^4$ and $R^5$ may be linked to form a cycle. In preferred embodiments, at least two of $R^2$, $R^3$, $R^4$ and $R^5$ are linked to form a cycle, such that the compound is a cyclic guanidine compound.

For example, $R^2$, $R^3$, $R^4$ and $R^5$ are independently selected from substituted or unsubstituted $C_1$-$C_{30}$ alkyl, $C_2$-$C_{30}$ alkenyl, $C_2$-$C_{30}$ alkynyl, $C_5$-$C_{30}$ aryl, $C_6$-$C_{30}$ aralkyl, and $C_6$-$C_{30}$ alkaryl, any of which may be heteroatom-containing. As mentioned previously, the alkyl, alkenyl, and alkynyl groups include linear, branched, and cyclic such groups. The aryl, aralkyl, and alkaryl groups include multicyclic groups such as annulated and linked ring systems.

In some embodiments of formula (I), $R^2$ and $R^3$ are taken together to form a cycle, and $R^4$ and $R^5$ are taken together to form a cycle, such that an annulated ring system is formed. Preferred embodiments include compounds having the structure of formula (Ia)

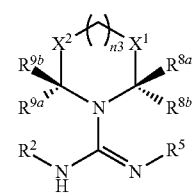

(Ia)

wherein
n1 and n2 are independently selected from zero and 1; and
$R^{6a}$, $R^{6b}$, $R^{6c}$, $R^{6d}$, $R^{7a}$, $R^{7b}$, $R^{7c}$, and $R^{7d}$ are independently selected from H, substituted or unsubstituted $C_1$-$C_{30}$ alkyl, $C_2$-$C_{30}$ alkenyl, $C_2$-$C_{30}$ alkynyl, $C_5$-$C_{30}$ aryl, $C_6$-$C_{30}$ aralkyl, and $C_6$-$C_{30}$ alkaryl, any of which may be may be heteroatom-containing, provided that any two of $R^{6a}$, $R^{6b}$, $R^{6c}$, $R^{6d}$, $R^{7a}$, $R^{7b}$, $R^{7c}$, and $R^{7d}$ may be taken together to form a ring.

In some embodiments of formula (Ia), n1 is zero and n2 is 1. In some embodiments of formula (Ia), n2 is zero and n1 is 1. In some embodiments of formula (Ia), n1 and n2 are both zero. In some embodiments of formula (Ia), n1 and n2 are both 1.

In some embodiments of formula (Ia), one of $R^{6a}$ and $R^{6b}$ is $C_5$-$C_{30}$ aryl, and the other is H, and one of $R^{7a}$ and $R^{7b}$ is $C_5$-$C_{30}$ aryl, and the other is H. In some such embodiments, the $C_5$-$C_{30}$ aryl group is phenyl.

In some embodiments of formula (Ia), $R^{6c}$, $R^{6d}$, $R^{7c}$, and $R^{7d}$ are each H. Examples of such embodiments include the following compounds:

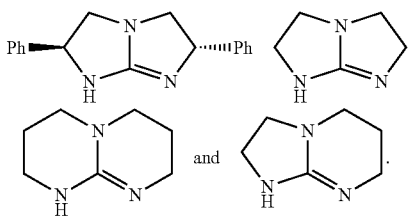

In some embodiments of formula (I), $R^3$ and $R^4$ are taken together to form a cycle. For example, preferred embodiments include compounds having the structure of formula (Ib)

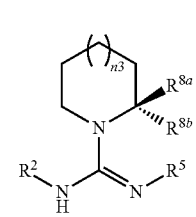

(Ib)

wherein
n3 is selected from 0 and 1;
$X^1$ and $X^2$ are independently selected from —$NR^{10}$— and —$C(R^{11})(R^{12})$—, wherein $R^{10}$, $R^{11}$, and $R^{12}$ are independently selected from H and alkyl; and
$R^{8a}$, $R^{8b}$, $R^{9a}$, and $R^{9b}$ are independently selected from alkyl, aryl, aralkyl, and alkaryl, provided that any two of $R^{8a}$, $R^{8b}$, $R^{9a}$, $R^{9b}$, $R^{10}$, $R^{11}$, and $R^{12}$ may be taken together to form a cycle.

In some embodiments of formula (Ib), $R^{9a}$ and $R^{9b}$ are both H, and $X^1$ and $X^2$ are both —$CH_2$—, such that the compounds have the structure of formula (Ic)

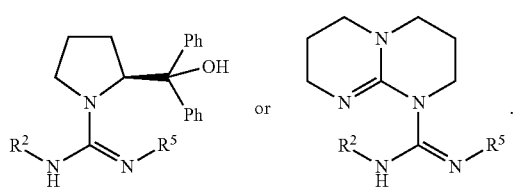

(Ic)

Further examples of embodiments of formula (Ib) include compounds having the structures

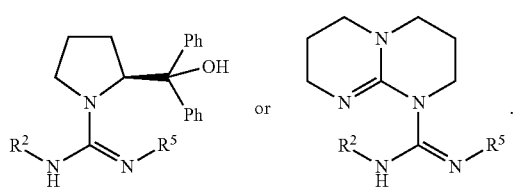

In some embodiments of the structures shown above, $R^2$ and $R^5$ are independently selected from substituted or unsubstituted $C_1$-$C_{30}$ alkyl and substituted or unsubstituted heteroatom-containing $C_1$-$C_{30}$ alkyl. For example, $R^2$ and $R^5$ may be $C_3$-$C_{30}$ alicyclic, such as cyclopropyl, cyclobutyl, cyclopentyl, cyclohexyl (Cy), cycloheptyl, or cyclooctyl. Also for example, $R^2$ and $R^5$ may be methyl, ethyl, propyl (i-propyl, n-propyl), or butyl (t-butyl, n-butyl, sec-butyl), or may be heteroatom-containing such as 3-dimethylaminopropyl or a salt thereof.

In some embodiments, the guanidine-containing compounds described herein are chemically more stable than other catalysts capable of causing depolymerization, such as N-heterocyclic carbene catalysts. In some embodiments, compared with N-heterocyclic carbene catalysts under similar conditions, the guanidine-containing compounds decompose at a substantially lower rate. Preferred catalysts are substantially stable under some or all of the depolymerization conditions described herein.

The guanidine-containing compounds described herein may be synthesized by any appropriate method, and such methods are readily ascertainable from the relevant literature. For example, cyclic guanidines may be prepared using the methods disclosed in U.S. Pat. No. 4,797,487, "Production of Bicyclic Guanidines from Bis(aminoalkyl)amine." It will be appreciated that the handling of certain guanidine-containing compounds may require precautions to avoid decomposition. For example, mixing of the reaction components may require an inert atmosphere.

The depolymerization catalysts of the disclosure (i.e., guanidine-containing compounds) are typically present in the reaction mixture in an amount (i.e., a "catalyst loading") that is less than 20 mol %, or less than 15%, or less than 10 mol %, or less than 5 mol %, or less than 2 mol %, or less than 1 mol %, or less than 0.5 mol %, or less than 0.1 mol %. Such catalyst loadings are measured as mol % relative to the total amount of monomer units present in the polymer sample at the beginning of the reaction.

The depolymerization reaction may be carried out in an inert atmosphere or in air (e.g., atmospheric conditions). In carrying out the reactions, combination of the reactants may be accomplished in any order. For example, the reactants can be combined by dissolving a catalytically effective amount of the selected catalyst in a solvent, combining the polymer and the catalyst solution, and then adding the nucleophilic reagent. In a particularly preferred embodiment, the polymer, the nucleophilic reagent, and the catalyst are combined and dissolved in a suitable solvent, and depolymerization thus occurs in a one-pot, one-step reaction.

The reaction mixture is typically, although not necessarily, agitated (e.g., stirred), and the progress of the reaction can be monitored by standard techniques, although visual inspection is generally sufficient, insofar as a transparent reaction mixture indicates that the polymer has degraded to an extent sufficient to allow all degradation products to dissolve. Examples of solvents that may be used in the depolymerization reaction include organic, protic, or aqueous solvents that are inert under the depolymerization conditions, such as aromatic hydrocarbons, chlorinated hydrocarbons, ethers, aliphatic hydrocarbons, or mixtures thereof. Preferred solvents include toluene, methylene chloride, tetrahydrofuran, methyl t-butyl ether, Isopar, gasoline, and mixtures thereof. Alternatively, the reaction can be performed without a solvent. Reaction temperatures are in the range of about 0° C. to about 200° C. When the reactions are carried out in solution, reaction temperatures are typically less than about 100° C., such as at most 80° C., or 50° C. or lower, or 30° C. or less. In one preferred embodiment, the reaction temperature is that of ambient conditions (i.e., room temperature). When the reactions are carried out in the melt (i.e., no solvent), temperatures are typically between about 120° C. and 200° C., such as <about 180° C., or between 120° C. and 180° C. The reaction time will generally, although again not necessarily, be in the range of about 1 to 48 hours, or from about 1 to 24 hours, or from about 12 to 24 hours, or less than 24 hours, or less than 12 hours. For example, excess ethylene glycol with the catalyst at elevated temperatures can be used to revert PET back to BHET.

The methods of the disclosure allow for the depolymerization of a polymer starting material to provide a depolymerization product that is substantially free of metal contaminants. In one embodiment, the depolymerization reaction provides a depolymerization product that has a concentration of metal contaminant equal to or less than the concentration of metal contaminant in the polymer starting material. For example, in the case of PET originally prepared using a metal catalyst and having a residual metal contaminant concentration, depolymerization using a monohydric alcohol and a cyclic guanidine catalyst according to the methods disclosed herein provides a depolymerization product consisting of a terephthalate ester, and an alcohol. The depolymerization product also contains the cyclic guanidine catalyst and the metal contaminant originally present in the polymer starting material. Further such examples and description are provided below.

The depolymerization products of the reactions of the disclosure typically, although not necessarily, comprise small molecules that are suitable to act as monomers in polymerization reactions. For example, in the depolymerization of PET according to the methods of the disclosure, the depolymerization products comprise an ester of teraphthalic acid (e.g., dimethyl terephthalate, diethyl terephthalate, and the like). Depolymerization products include a variety of monomers that may be used to prepare new polymers, such as polymers with amide, urethane, urea, benzimidazole, benzoxazole, and ester linkages. It will be appreciated that the identity of the depolymerization product ester is a function of the reactants—i.e., the identity of the nucleophilic reagent and the polymer. Accordingly, the disclosure provides a method for preparing a polymerizable monomer, the method comprising depolymerizing a polymer to form the monomer as a depolymerization product. The methods of the disclosure may, where desired, further involve forming new polymer or monomer materials using the depolymerization products generated by the depolymerization reactions.

As an example, the depolymerization products that result when PET is depolymerized with benzyl 3-aminopropanoate according to the methods disclosed herein may be further reacted in a hydrolysis reaction as shown in Scheme 1.

Scheme 1

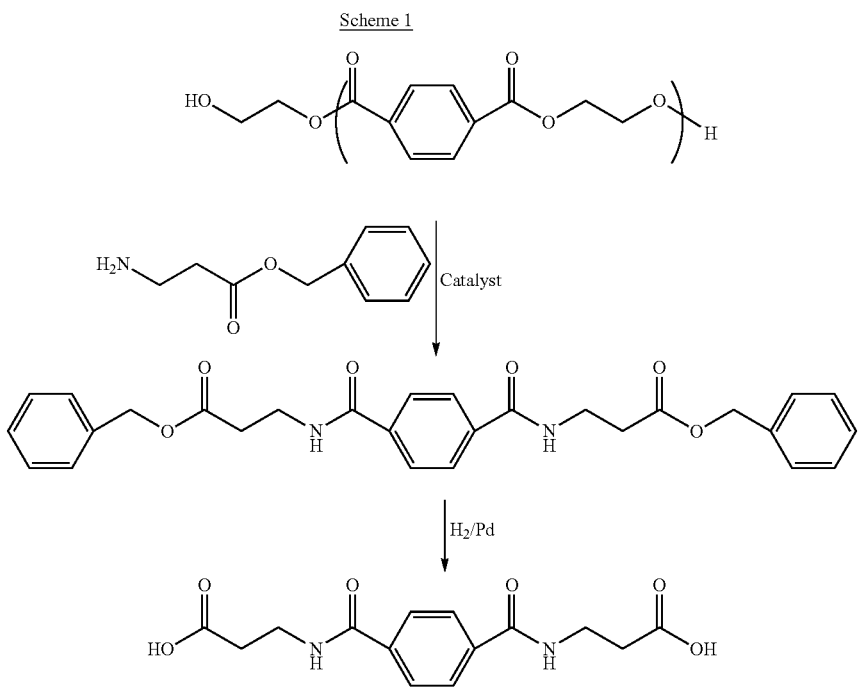

Because the depolymerization catalysts disclosed herein do not contain metals, the depolymerization products are substantially free of metal contaminants. In particular, the concentration of metal contaminants in the depolymerization products is equal to or less than the concentration of metal contaminants in the polymer prior to depolymerization. For example, when a sample of PET is depolymerized according to the invention, and the sample of PET has a certain concentration of metal contaminant (e.g., residual metal catalyst from the initial polymerization reaction that was used to prepare the PET), the depolymerization reaction does not increase the total concentration of metal contaminants. The depolymerization products (e.g., bis(hydroxy ethylene) terephthalate, or BHET) contain the same or lower concentration of metal contaminants. A lower concentration of metal contaminant may be observed if the depolymerization products are subjected to any purification steps (such as distillation, recrystallization, chromatography, etc.). As a further example, a sample of PET having no metal contaminants (or an undetectable level of metal contaminants) may be depolymerized according to the invention to yield depolymerization products having no metal contaminants (or an undetectable level of metal contaminants).

For example, depending on the method of manufacture, PET used for drinking bottles may have a residual metal contamination level of <50 ppm, or <20 ppm, or <5 ppm, or below 1 ppm. In some embodiments, the methods of the invention provide "bottle-to-bottle" recycling since the level of metal contamination of the depolymerization products that result from treating such PET by a method of the invention will be no higher than the level of metal contamination of the original polymer. Thus, in some embodiments, the methods of the invention provide depolymerization products having a metal contamination concentration of <50 ppm, or <20 ppm, or <5 ppm, or below 1 ppm.

The methods described herein find utility, for example, in the recycling of polymers, the minimization of solid waste, the preparation of polymerization feedstock, and similar areas as described herein throughout.

All patents, patent applications, and publications mentioned herein are hereby incorporated by reference in their entireties; however, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description as well as the examples that follow, are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

EXAMPLE 1

TBD decomposed PET taken from a commercial water bottle as follows: in a small reaction flask, a 250 mg square of PET was immersed in toluene (1 ml). Twenty drops of methanol and 25 mg of 1,5,7-triazabicyclo[4.4.0]dec-5-ene (TBD) were added, and the mixture was left to stand overnight at room temperature. Over time, the PET square disintegrated. The final solution was diluted with methylene chloride, extracted with water and concentrated. The product was identified as dimethylterephthalate by its two definitive peaks in its $^1$H-NMR spectrum.

EXAMPLE 2

PET film (0.2 g) was added to a small flask and suspended in a mixture of toluene/methanol (60/40 mixture) 1.5 mL total. TBD (0.012 g) was added and allowed to stir overnight at room temperature. Once the suspended film became homogeneous (24 hours), the reaction was judged complete. The reaction was concentrated by rotary evaporation. The crude product was dissolved in 50 ml of methylene chloride and extracted with weak acid and then water. The compound in the methylene chloride phase was dried and concentrated. The resulting white powder was characterized my NMR and showed a high purity DMT.

EXAMPLE 3

PET was depolymerized according to Scheme 2.

In a schlenk flask, freshly cut polyethylene terephthalate slices (PET: 3 mm.times.3 mm) and 10 weight excess of ethylene glycol (EG) are add to various amounts of triazabicyclodecene (TBD). The weight percentage of TBD with respect to PET ranges from 0.036 to 0.29. The schlenk flask is then sealed and immersed in a 185° C. oil bath. The thermal degradation procedure is considered complete after visual disappearance of all PET slices. FIG. 1 represents the evolution of recorded degradation times required for a complete dissolution of PET with respect to the weight amounts of used TBD. When the thermal degradation is complete, the medium is cooled down and analyzed by $^1$H-NMR (in CDCl$_3$) and GPC.

EXAMPLES 4-6

In Examples 4-6, PET is depolymerized as shown in the Scheme 3.

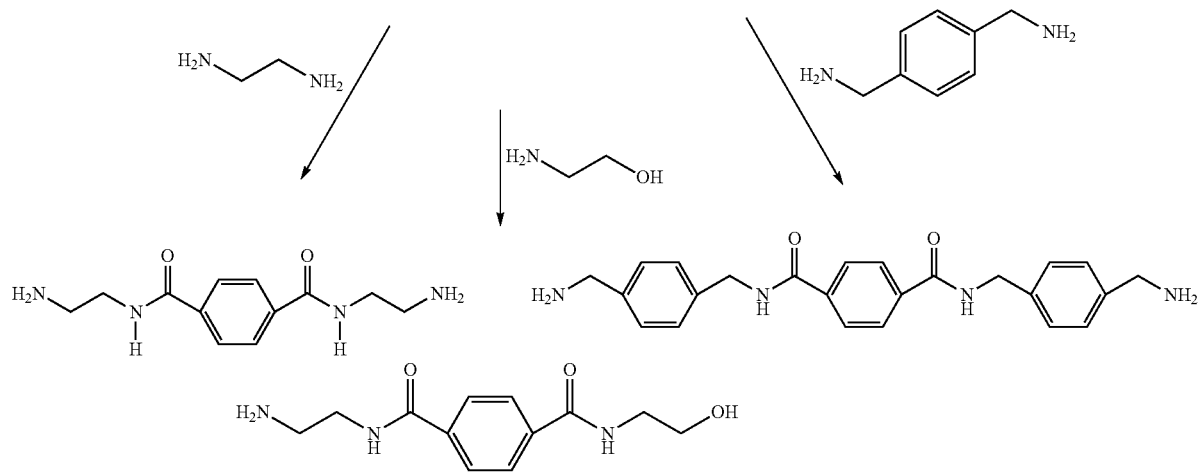

Scheme 3

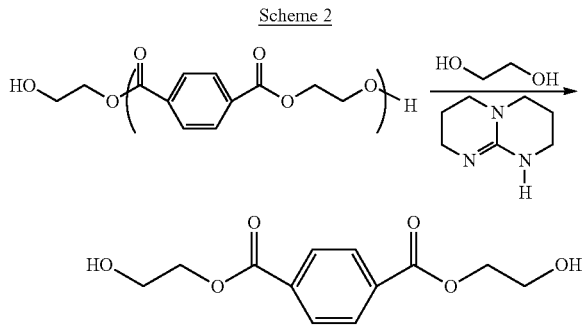

Scheme 2

EXAMPLE 4

A schlenk flask was charged with polyethylene terephthalate (PET) 400 mg (pieces cut from a bottle 3.times.3 mm), TBD 35 mg, and ethanolamine 1.8 g. The flask was evacuated for 15 min, sealed under vacuum, placed in an oil bath at 170° C., and allowed to react for 4 hours. The reaction was cooled and the resulting amide monomer crystallized from the excess solution of diamine. Ethyl acetate was added to remove by-products; the product was isolated by filtration, rinsed several times with ethyl acetate, and dried. Analysis by NMR of the final product confirmed the following structure:

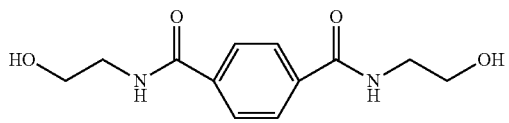 [SMILES: O=C(NCCO)c1ccc(C(=O)NCCO)cc1]

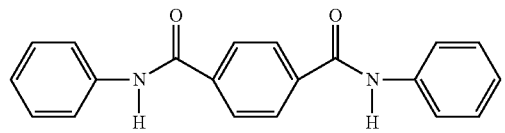

EXAMPLE 5

A schlenk flask was charged with polyethylene terephthalate (PET) 400 mg (pieces cut from a bottle 3.times.3 mm), TBD 35 mg, and ethylene diamine 1.8 g. The flask was evacuated for 15 min, sealed under vacuum, placed in an oil bath at 130° C. (boiling point of ethylene diamine=127° C.), and allowed to react for 5 hours. The reaction was cooled and the resulting amide monomer crystallized from the excess solution of diamine. Ethyl acetate was added to remove by-products, the product was isolated by filtration, rinsed several times with ethyl acetate, and dried. Analysis by NMR of the final product confirmed the following structure:

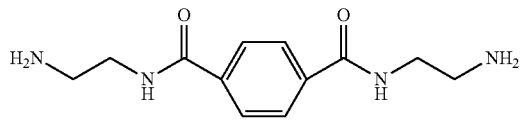 [SMILES: NCCNC(=O)c1ccc(C(=O)NCCN)cc1]

EXAMPLE 6

A schlenk flask was charged with polyethylene terephthalate (PET) 400 mg (pieces cut from a bottle 3.times.3 mm), TBD 35 mg, and 4-aminobenzyl amine 1.8 g. The flask was evacuated for 15 min, sealed under vacuum, placed in an oil bath at 150° C., and allowed to react for 7 hours. The reaction was cooled and the resulting amine monomer crystallized from the excess solution of starting diamine. Ethyl acetate was added to remove by-products; the product was isolated by filtration, rinsed several times with ethyl acetate, and dried. Analysis by NMR of the final product confirmed the following structure:

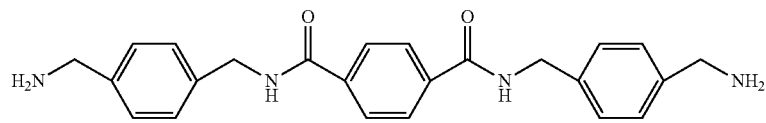 [SMILES: NCc1ccc(CNC(=O)c2ccc(C(=O)NCc3ccc(CN)cc3)cc2)cc1]

EXAMPLE 7

A schlenk flask was charged with polyethylene terephthalate (PET) 400 mg (pieces cut from a bottle 3.times.3 mm), TBD 35 mg, and aniline 2 g. The flask was evacuated for 10 min, sealed under vacuum, placed in an oil bath at 150° C., and allowed to react for 20 hours. The reaction was cooled and the resulting amide monomer crystallized from the excess solution of diamine. Ethyl acetate was added to remove all by-products; the product was isolated by filtration, rinsed several times with ethyl acetate, and dried. Analysis by NMR of the final product confirmed the following structure:

EXAMPLE 8

A sample of PET from a commercial water bottle (0.1 g) was dried in a vacuum oven and added to a small flask and suspended in 5 mL of THF. 1,4,6-triazabicyclo[3.3.0]-oct-4-ene (TBO) (0.019 g) and 0.01 mL of MeOH was added and allowed to stir at room temperature. The resulting cloudy mixture contained a mixture of PET and dimethyl terephthalate.

EXAMPLE 9

Synthesis of 1,4,6-triazabicyclo[3.3.0]-oct-4-ene (TBO)

With stirring at room temperature under nitrogen atmosphere, xylenes (300 mL), diethylenetriamine (20.6 g, 21.7 mL, 0.2 mol), and carbon disulfide (15.2 g, 12.0 mL, 0.2 mol) were added to a three-necked flask. A white precipitate formed immediately and the suspension was heated to reflux. Evolution of $H_2S$ from the reaction exhaust was monitored using filter paper soaked in a methanolic suspension of lead (II) acetate. After 10 days of reflux under nitrogen, GC/MS analysis confirmed quantitative conversion to the target compound. Upon cooling to room temperature a white solid crystallized from solution, and the supernatant was decanted. The solid was washed with 2.times.50 mL portions of acetone and pentane, respectively, and dried under vacuum overnight. (8.65 g, 39%). $^1H$ NMR 400 MHz ($CDCl_3$) δ (ppm)=6.02 [br s, $^1H$, N—H], 3.79 [t, 2H, backbone $CH_2$, J=7.0 Hz], 3.05 [t, 2H, backbone $CH_2$, J=7.0 Hz]. $^{13}C$ NMR 100.6 MHz ($CDCl_3$) δ (ppm)=171.18 [central $sp^2$ C], 52.62 [backbone $CH_2$], 49.38 [backbone $CH_2$]. LRMS (m/z): 112.1 (positive ion, M+H).

EXAMPLE 10

Synthesis of Guanidine Catalysts

The general procedure for the synthesis of the guanidine catalysts described herein is shown in Scheme 4.

Scheme 4

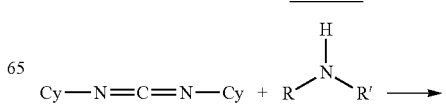

-continued

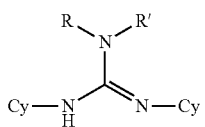

DCC was reacted neat (110° C.) with a secondary amine. Once the DCC melted a homogeneous solution was formed and the reaction was allowed to proceed overnight to generate a viscous oil/gel. The reaction was followed by GC/MS and quantitative conversion of starting material was accomplished in ~12 hours. Compounds were purified either by kugelroh distillation or by column chromatography.

SYNTHESIS OF GUANIDINIUM 1: Dicyclohexylcarbodiimide (3 g, 14.8 mmol) and pyrrolidine (10 ml, 120 mmol) were heated to reflux overnight under $N_2$. The excess pyrrolidine was distilled off and the product was purified by Kugelroh distillation (265° C.) to yield a colorless oil. The product guanidine compound has the structure shown below.

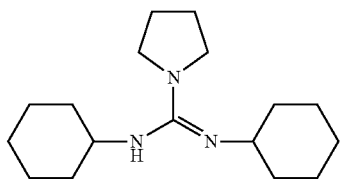 [SMILES: C1CCC(/N=C(/NC2CCCCC2)N2CCCC2)CC1]

SYNTHESIS OF GUANIDINIUM 2: DCC (0.93 g, 4.52 mmol) and TBD (0.66 g, 4.76 mmol) were allowed to react for 20 (125° C. under $N_2$). The gel like product was purified by Kugelroh distillation 265° C. to yield a white crystalline solid $T_m$=69-71° C. The product guanidine compound has the structure shown below.

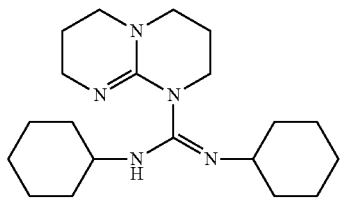 [SMILES: C1CCC(/N=C(/NC2CCCCC2)N2CCCN3CCCN=C32)CC1]

SYNTHESIS OF GUANIDINIUM 3: DCC (0.70 g, 3.39 mmol) and (s)-(−) α,α-diphenyl-2-pyrrolidinemethanol (0.86 g, 3.39 mmol) were heated (under $N_2$) at 80° C. for 20 h. Temperatures above 100° C. resulted in decomposition. The product was purified using column chromatographs (ethyl acetate/hexane (60/40)) to yield a white crystalline solid $T_m$=104-106° C. The product guanidine compound has the structure shown below.

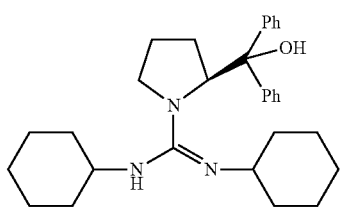 [SMILES: OC(c1ccccc1)(c1ccccc1)[C@@H]1CCCN1/C(=N\C1CCCCC1)NC1CCCCC1]

We claim:

1. A composition comprising a polymer, a nucleophilic compound, and a guanidine-containing compound, wherein the polymer has a backbone comprising a repeat unit with an electrophilic linkage, wherein the guanidine-containing compound has the structure of formula (Ib)

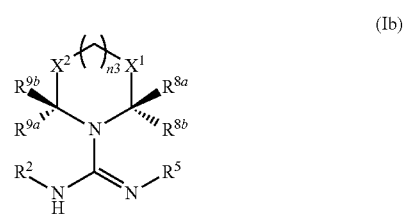

wherein n3 is selected from 0 and 1;

$R^2$ and $R^5$ are independently selected from hydrogen, $C_1$-$C_{30}$ hydrocarbyl, substituted and unsubstituted $C_1$-$C_{30}$ alkyl, and substituted and unsubstituted heteroatom-containing $C_1$-$C_{30}$ alkyl;

$X^1$ and $X^2$ are independently selected from —$NR^{10}$— and —$C(R^{11})(R^{12})$—, wherein $R^{10}$, $R^{11}$, and $R^{12}$ are independently selected from H and alkyl; and $R^{8a}$, $R^{8b}$, $R^{9a}$, and $R^{9b}$ are independently selected from hydrogen and substituted and unsubstituted alkyl, aryl, aralkyl, and alkaryl, any of which may be heteroatom-containing, provided that any two of $R^{8a}$, $R^{8b}$, $R^{9a}$, $R^{9b}$, $R^{10}$, $R^{11}$, and $R^{12}$ may be taken together to form a cycle.

2. The composition of claim 1, wherein the nucleophilic compound comprises at least one hydroxyl group, at least one amine group, or a combination thereof.

3. The composition of claim 1, wherein the nucleophilic compound comprises one or more nucleophilic groups selected from hydroxyl, ether, carboxylato, amine, azide, and sulfhydryl.

4. The composition of claim 1, wherein the nucleophilic compound comprises two hydroxyl groups, two amine groups, or one hydroxyl group and one amine group.

5. The composition of claim 1, wherein the nucleophilic compound corresponds to the electrophilic linkage in the polymer backbone, such that nucleophilic attack at the electrophilic linkage results in cleavage of the linkage.

6. The composition of claim 5, wherein the ratio of the nucleophilic compound to the electrophilic linkage is 1:1.

7. The composition of claim 5, wherein the nucleophilic compound is in excess of the electrophilic linkage.

8. The composition of claim 1, wherein the guanidine-containing compound is present in an amount effective to cause reaction of the electrophilic linkage with the nucleophilic compound.

9. The composition of claim 1, wherein the guanidine-containing compound has a structure selected from:

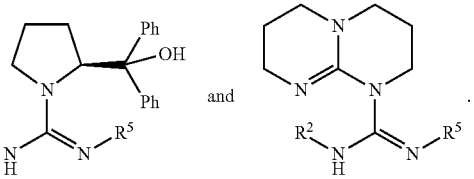

10. The composition of claim 1, wherein the electrophilic linkage is selected from ester linkages, carbonate linkages, urethane linkages, substituted urethane linkages, phosphate linkages, amido linkages, substituted amido linkages, thioester linkages, sulfonate ester linkages, and combinations thereof.

11. The composition of claim 10, wherein the electrophilic linkages comprise ester linkages, such that the polymer is a polyester.

12. The composition of claim 1, wherein the repeat unit further comprises a linker moiety comprising a $C_1$-$C_{30}$ hydrocarbylene group.

13. The composition of claim 12, wherein the linker moiety is selected from the group consisting of substituted and unsubstituted $C_1$-$C_{30}$ alkylene, $C_2$-$C_{30}$ alkenylene, $C_2$-$C_{30}$ alkynylene, $C_5$-$C_{30}$ arylene, $C_6$-$C_{30}$ alkenylene, and $C_6$-$C_{30}$ aralkylene.

14. The composition of claim 12, wherein the linker moiety is selected from the group consisting of thioether, ether, and amino groups.

15. The composition of claim 1, wherein the polymer comprises monomer units, and wherein the guanidine-containing compound is present in an amount less than about 20 mol% relative to the amount of monomer units present.

\* \* \* \* \*